United States Patent
Zhang et al.

(10) Patent No.: US 10,369,040 B2
(45) Date of Patent: *Aug. 6, 2019

(54) LAYERED SOFT PALATE SUPPORT AND IMPLANTATION METHOD

(71) Applicant: GUANGZHOU T.K. MEDICAL INSTRUMENT CO. LTD., Guangzhou, Guangdong (CN)

(72) Inventors: Xiangmin Zhang, Guangzhou (CN); Xing Zhou, Guangzhou (CN)

(*) Notice: Subject to any disclaimer, the term of this patent is extended or adjusted under 35 U.S.C. 154(b) by 341 days.

This patent is subject to a terminal disclaimer.

(21) Appl. No.: 15/236,104

(22) Filed: Aug. 12, 2016

(65) Prior Publication Data

US 2016/0346114 A1    Dec. 1, 2016

Related U.S. Application Data

(63) Continuation of application No. 14/000,598, filed as application No. PCT/CN2012/075238 on May 9, 2012, now Pat. No. 9,445,935.

(30) Foreign Application Priority Data

Jun. 22, 2011  (CN) .......................... 2011 1 0169918

(51) Int. Cl.
  *A61F 5/56*  (2006.01)
(52) U.S. Cl.
  CPC .................................. *A61F 5/566* (2013.01)
(58) Field of Classification Search
  CPC ...... A61F 5/566; A61F 5/56; A61F 2005/563; A61F 2/20; A61F 2/00; A61F 5/08; A61C 7/08

See application file for complete search history.

(56) References Cited

U.S. PATENT DOCUMENTS

| 9,445,935 | B2* | 9/2016 | Zhang | A61F 5/566 |
| 2007/0246052 | A1* | 10/2007 | Hegde | A61F 5/56 |
| | | | | 128/848 |

(Continued)

FOREIGN PATENT DOCUMENTS

| CA | 2747842 A1 | 5/2010 |
| CN | 1720881 A | 1/2006 |

(Continued)

OTHER PUBLICATIONS

Xiangmin Zhang, International Search Report, PCTCN2012/075238, dated Aug. 23, 2012, 6 pages.

(Continued)

*Primary Examiner* — Ophelia A Hawthorne
(74) *Attorney, Agent, or Firm* — Morgan, Lewis & Bockius LLP

(57) ABSTRACT

The present invention relates to a layered soft palate support and an implantation method for treating sleep apnea/hypopnea syndrome or snoring. The layered soft palate support is a layered structure formed by two or more supporting plates. The layered soft palate support has a hard palate connecting end and a soft palate insertion end, where the soft palate insertion end is configured for insertion into a soft palate, and the hard palate connecting end is configured to be fixed to a hard palate. At least two of the two or more supporting plates have distinct lengths with respect to a longitudinal axis.

20 Claims, 12 Drawing Sheets

(56) References Cited

U.S. PATENT DOCUMENTS

| | | | |
|---|---|---|---|
| 2008/0046022 | A1 | 2/2008 | Bhat et al. |
| 2009/0078275 | A1* | 3/2009 | Hegde .................. A61B 5/0031 |
| | | | 128/848 |
| 2010/0037901 | A1 | 2/2010 | Rousseau et al. |
| 2010/0163056 | A1 | 7/2010 | Tschopp et al. |
| 2010/0234946 | A1 | 9/2010 | Rousseau |

FOREIGN PATENT DOCUMENTS

| | | | |
|---|---|---|---|
| CN | 201320227 | Y | 10/2009 |
| CN | 101732108 | A | 6/2010 |
| CN | 102028559 | A | 4/2011 |
| EP | 2332496 | A1 | 6/2011 |
| EP | 2724689 | A1 | 4/2014 |
| JP | 2009-534132 | T | 9/2009 |
| WO | WO 2008097890 | A2 | 8/2008 |
| WO | WO 2010054603 | A1 | 5/2010 |
| WO | WO 2010068251 | A1 | 6/2010 |

OTHER PUBLICATIONS

Xiangmin Zhang, Extended European Search Report, EP12803487.3, dated Feb. 5, 2015, 6 pages.

Xiangmin Zhang, Communication Pursuant to Rules 70(2) and 70a(2) re:Response to Search Apinion, EP12803487.3, dated Feb. 25, 2015, 1 pg.

Xiangmin Zhang, Invitation to file search resuts or a statement of non-availability pursuant to Rule 70b(1) EPC, EP12803487.3, dated Sep. 8, 2015, 1 pg.

Xiangmin Zhang, Communication Pursuant to Article 94-3, EP12803487.3, dated May 4, 2016, 4 pgs.

Xiangmin Zhang, Patent Examination Report No. 1, AU2012272407, dated Dec. 15, 2015, 3 pgs.

Xiangmin Zhang, Certificate of Grant, AU2012272407, dated Sep. 8, 2016, 1 pg.

Xiangmin Zhang, Certificate of Grant, SG2013087127, dated Aug. 23, 2016, dated Sep. 8, 2016, 1 pg.

Xiangmin Zhang, Notice of Reasons for Rejection, JP2014-516174, dated Dec. 22, 2015, 13 pgs.

Xiangmin Zhang, Notice of Reasons for Rejection, JP2014-516174, dated Oct. 3, 2016, 22 pgs.

Xiangmin Zhang, Notice of Allowance, CA2,837,810, dated May 1, 2017. 1 pg.

Xiangmin Zhang, Letters Patent, CA2,837,810, dated Nov. 28, 2017. 1 pg.

Xiangmin Zhang, Certificate of Patent, JP2014-516174, dated Jun. 16, 2017, 2 pgs.

Xiangmin Zhang, Substantive Examination Adverse Report, (MY) PI2013004597, dated Oct. 27, 2017, 3 pgs.

Xiangmin Zhang, Substantive Examination Clear Report, (MY) PI2013004597, dated Jun. 29, 2018, 2 pgs.

* cited by examiner

LAYERED SOFT PALATE SUPPORT AND IMPLANTATION METHOD

CROSS REFERENCE TO RELATED APPLICATIONS

This application is a continuation application of U.S. patent application Ser. No. 14/000,598, filed Aug. 20, 2013, entitled "Layered Soft Palate Support and Implantation Method," which is a national stage application of PCT/CN2012/075238, filed May 9, 2012, entitled "Soft Palate Support Having Layered Structure and Implanting Method," which claims priority to Chinese Patent Application No. 201110169918.5, filed Jun. 22, 2011, entitled "Layer Structural Soft Palate Supporting Body and Implanting Method Thereof," all of which are hereby incorporated by reference in their entirety.

BACKGROUND OF THE INVENTION

Field of the Invention

The present invention relates to a layered soft palate support, and more particularly to a layered soft palate support and an implantation method for treating adult obstructive sleep apnea/hypopnea syndrome (OSAHS).

Related Art

Adult OSAHS is a sleep breathing disorder with clinical features of snoring and apnea caused by upper airway collapse and obstruction during sleep. The morbidity of OSAHS is about 4% among adult men and about 2% among adult women even according to the lowest diagnosis criteria, and OSAHS presents a serious threat to the life and health of patients.

As for the pathogenesis of OSAHS, it is generally considered that the main cause is that, pharyngeal muscles for maintaining the upper airway open relax during sleep, resulting in soft tissue collapse and obstruction, and the plane of obstruction is usually located in the soft palate, tonsil, and tongue root. Many methods for treating OSAHS exist, which include two types, that is, non-surgical treatment and surgical treatment.

Methods of Non-Surgical Treatment Mainly Include:

1. Continuous Positive Airway Pressure (CPAP), in which a breathing machine capable of continuously generating a positive pressure is closely connected with the nose and face of a patient via a nasal mask, so as to prevent collapse and obstruction of the soft tissues of the airway during sleep. Though the method has a good effect, it is difficult for approximately ⅔ of the patients to adapt to the machine, and they cannot sleep when wearing the machine.

2. Oral appliance. A device is placed in an oral cavity to move forward the mandible or pull forward the tongue, so as to enlarge the pharyngeal cavity and release the airway obstruction during sleep. The method has many types and produces a certain effect, but most patients cannot adapt to it. The oral appliance leads to irritation and foreign body sensation, causing that the user cannot fall asleep, and may have temporo-mandibular joint injury with long term use.

Methods of Surgical Treatment Mainly Include:

1. Radiofrequency ablation, which is also referred to as low-temperature plasma radiofrequency ablation, and is a minimally invasive surgical method. An electrode is penetrated into the soft tissues which cause airway obstruction, such as the soft palate, tonsil, and tongue root, and is electrified to induce tissue coagulation, necrosis, fibrosis, and contraction by heating. The method has a certain therapeutic effect, is effective for a slight case, has a poor long-term efficacy, and is ineffective for serious patients.

2. Palatopharyngoplasty. Since Fujita improved the Palatopharyngoplasty of Ikematus, a Japanese scholar, into uvulopalatopharyngoplasty (UPPP) and introduced it to the US in 1981, various improved technologies based on UPPP, including Simmons method, Fairbanks method, Dickson method, Woodson method, Z-palatoplasty (ZPP), uvulopalatal flap (UPF), H-uvulopalatopharyngoplasty (H-UPPP) have been successively reported in literatures, which made a great contribution to symptom alleviation and recovery of OSAHS patients. Countless patients benefit from the surgical treatment solution. However, in terms of long-term effect, since the mucous membrane and soft palate tissue structure are excessively removed, functional muscles are injured, resulting in complications of nasal regurgitation during swallowing, rhinolalia aperta, and nasopharyngeal stenosis and atresia. It is the leading edge and focus for the research and development of OSAHS treatment technologies nowadays to develop a method and corresponding surgical instruments which create a smaller wound or perform surgical treatment in a minimally invasive manner.

Based on the above, though generating a certain effect, the existing technologies and methods for treating OSAHS and snoring still have many defects, and have a poor long-term effect. Therefore, it is necessary to develop a new method and design a new instrument to treat OSAHS and snoring, in which the new method should create a wound as small as possible, and the new instrument should be safe, effective, simple, and reliable.

SUMMARY OF THE INVENTION

Research reports and clinical experience indicate that, the relaxation and collapse of the soft palate portion is one of main causes of snoring and OSAHS. The inventor has disclosed, in PCT/CN2009/072328 and PCT/CN2009/074959, two soft palate supports of different structures and corresponding implantation methods. The principle of such technologies for treating OSAHS lies in that: supported by a hard palate, a support inserted into a muscular layer of a soft palate is used to lift the collapsed soft palate, thereby achieving the objective of minimally invasive surgical treatment of snoring and OSAHS. Since the support inserted into the muscular layer of the soft palate needs to swing along with the soft palate during swallowing, a high requirement is imposed on the fatigue resistance of the support. How to improve the fatigue resistance of the soft palate support becomes a key to the improvement of the service life of the soft palate support. The present invention is further improvement and optimization of the foregoing solutions, and mainly improves the fatigue life of the support.

The present invention provides a layered soft palate support is a flat implant made of a material capable of being implanted into a human body for a long term, and includes: a hard palate connecting end, configured with a connecting structure connected with a hard palate; and a support, being a layered structure formed by stacking two or more layers of supporting plates and capable of being inserted into a soft palate, and removably or irremovably fixed to the hard palate connecting end.

Further, the hard palate connecting end has a length $L1$ of 5 to 30 mm, the support has a length $L2$ of 15 mm to 60 mm, and a lifting angle β of the support, that is, an angle between a plane of the hard palate and a most distal end of the support, is 30° to 80°.

A bending radius R1 of a near end of the support, that is, close to the hard palate connecting end, is 10 mm to 100 mm; a bending radius R2 of a distal end of the support, that is, away from the hard palate connecting end, is 20 mm to 120 mm; and the near end of the support has a thickness δ1 of 0.5 mm to 1.8 mm, and the distal end has a thickness δ2 of 0.1 mm to 0.8 mm.

A sweepback angle γ of a warped end at a distal end of the support, that is, an angle γ between a plane of the supporting plate at the distal end of the support and a plane of the warped end, is 0° to 75°, and preferably 20° to 50°.

The supporting plate is a thin-walled plate made of a medical-purpose elastic material and having a curvature matching the shape of the soft palate, and the thin-walled plate has a thickness of 0.01 mm to 1.5 mm, and preferably 0.01 mm to 0.8 mm.

The supporting plate has a uniform or non-uniform wall thickness; and when the supporting plate has a non-uniform wall thickness, the larger the length of the supporting plate is, the larger the amplitude of swing is, and the smaller the wall thickness is.

The number M of layers of the thin-walled supporting plates stacked at a near end of the layered soft palate support (that is, close to the hard palate connecting end) is greater than the number N of layers of the thin-walled supporting plates stacked at a distal end of the layered soft palate support (that is, away from the hard palate connecting end).

In the support, the thin-walled supporting plates may be stacked in various manners stacked to form the layered structure, which are mainly as follows:

(1) The supporting plates of the layered structure are sequentially arranged in a descending order of length, front supporting plates, that is, the supporting plates close to teeth are long, and rear supporting plates, that is, the supporting plates close to a posterior pharyngeal wall are short.

(2) The supporting plates of the layered structure are sequentially arranged in an ascending order of length, front supporting plates, that is, the supporting plates close to teeth are short, and rear supporting plates, that is, the supporting plates close to a posterior pharyngeal wall are long.

(3) The supporting plates of the layered structure are arranged in a sandwiched configuration, the length of a frontmost supporting plate is near or equal to the length of a rearmost supporting plate, and intermediate supporting plates are sequentially arranged in a descending order of length, are symmetrically arranged or are sequentially arranged in an ascending order of length.

(4) When the supporting plates of the layered structure are arranged in a sandwiched configuration, the frontmost supporting plate and the rearmost supporting plate are formed by bending a single plate into a U-shape, and the intermediate supporting plates are sequentially arranged in a descending order of length, are symmetrically arranged or are sequentially arranged in an ascending order of length.

In addition, the supporting plate is configured with through holes, for facilitating growth and coverage of tissues, to fix the support into the muscular layer of the soft palate.

Further, the layered soft palate support includes a blunt edge. The blunt edge may be designed in various ways, which are mainly as follows:

The blunt edge is a coil spring structure, wound in through holes at an edge of the supporting plate, to connect the supporting plates.

The layered soft palate support includes a blunt edge and the blunt edge includes more than one coil spring segment, wound in through holes of the supporting plate, to connect the supporting plates.

The blunt edge is a rivet-type structure or a concave-convex position-limiting engagement structure.

The layered soft palate support includes a position-limiting mechanism for limiting a distance between the layers of the supporting plates of the layered support, the supporting plates are constrained by the position-limiting mechanism, the supporting plate has a variable degree of curvature, a gap between the layers of the supporting plates is limited by the position-limiting mechanism, and the gap is smaller than 2 mm. The limiting mechanism may be designed in various ways, which are mainly as follows:

(1) The limiting mechanism is a locking pin of a concave-convex position-limiting engagement structure, and formed by a lock nut and a pin.

(2) The limiting mechanism is formed by a limiting groove and a limiting plate, and the limiting plate is part of an edge of one of the supporting plates, and is bent to form a rectangular or U-shaped slot opening serving as the limiting groove.

The layered soft palate support includes an adjustment mechanism capable of adjusting the degree of curvature of the supporting plate. The adjustment mechanism may be designed in various ways, which are mainly as follows:

(1) The adjustment mechanism is a wedge-shaped adjustment mechanism. The degree of curvature of the support can be changed by adjusting the wedge-shaped adjustment mechanism. When the wedge-shaped adjustment mechanism is moved toward a near end, the degree of curvature of the support is increased, so as to increase a lifting degree of the soft palate; and when the wedge-shaped adjustment mechanism is moved toward a distal end, the degree of curvature of the support is reduced, so as to reduce the lifting degree of the soft palate.

(2) The adjustment mechanism is an adjustment washer. When the height of the adjustment washer is increased, the degree of curvature of the support is increased, so as to increase a lifting degree of the soft palate; and when the height of the adjustment washer is reduced, the degree of curvature of the support is reduced, so as to reduce the lifting degree of the soft palate.

The medical-purpose elastic material of the supporting plate is selected from a group consisting of amorphous alloy (also referred to as metallic glass), titanium-zirconium-niobium alloy, titanium-nickel shape memory alloy, titanium and titanium alloy, medical grade stainless steel, and medical grade elastic non-metallic materials.

Further, the amorphous alloy has excellent elasticity and excellent fatigue resistance, and is selected from a group consisting of Ti-based amorphous metal materials, Zr-based amorphous metal materials, Nb-based amorphous metal materials, and Fe-based amorphous metal materials.

The connecting structure of the hard palate connecting end is a through hole through which the hard palate connecting end is fixed to the hard palate by using a screw. The connecting structure of the hard palate connecting end generally adopts a through hole structure, and through the through hole, the hard palate connecting end can be fixed to the hard palate by using a screw.

In addition, the hard palate connecting end includes a fixing rivet for riveting the supporting plates located at the hard palate connecting end, to facilitate product mounting.

The implantation method of the layered soft palate support according to the present invention is: making a small incision at a junction of a soft palate and a hard palate, and inserting a support into a muscular layer at a middle portion of the soft palate; and passing a medical bone nail through a through hole on a hard palate connecting end to fix the hard palate connecting end to the hard palate.

The support is inserted into the soft palate by a length equal to ⅕ to ⅘, and most preferably, ⅔ to ¾, of a total length of the soft palate.

Further, the layered soft palate support may be implanted in two stages. In a first stage, the hard palate connecting end of the layered soft palate support is implanted first, and the bone nail is passed through the through hole on the hard palate connecting end to fix the hard palate connecting end to the hard palate; and one month to three months later, the hard palate connecting end is firmly fixed to the hard palate, and at this time, a second stage surgery is performed: making a small incision at the junction of the soft palate and the hard palate, inserting one end of the support into the muscular layer at the middle portion of the soft palate, and fixing the other end of the support to the hard palate connecting end.

The present invention relates to a layered soft palate support and an implantation method for treating sleep apnea/hypopnea syndrome or snoring. The layered soft palate support is a flat implant made of a material capable of being implanted into a human body for a long term, and includes a hard palate connecting end and a support. The support is a layered structure formed by stacking two or more layers of supporting plates and capable of being inserted into a soft palate, and is removably or irremovably fixed to the hard palate connecting end. The hard palate connecting end is configured with a connecting structure connected with a hard palate, and the hard palate connecting end is fixed to the hard palate through the connecting structure. The support is implanted into a muscular layer of the soft palate, and is inserted into the soft palate by a length equal to ⅕ to ⅘ of a total length of the soft palate.

The use of the layered structure formed by stacking thin-walled plates not only improves the adaptability of the support but also significantly improves the fatigue fracture resistance of the support while ensuring the supporting force.

Since the layered soft palate support can effectively lift the soft palate collapsing during sleep and relieve an upper airway obstruction condition, objectives of treating OSAHS and snoring can be achieved.

Clinical application has proved that, the method and implanted instrument of the present invention have the advantages of small wound, few complications, reliable efficacy, and great comfort, thereby realizing the objective of minimally invasive treatment.

In particular, for implantation of the layered soft palate support of the present invention, during clinical implantation, the degree of curvature of the support is adjusted as required by adjusting the position of the wedge-shaped adjustment mechanism or by adjusting the height of the adjustment washer, so that the lifting degree of the soft palate being supported can be adjusted within a certain range, so as to achieve optimal treatment effect and comfort.

BRIEF DESCRIPTION OF THE DRAWINGS

FIG. 9-1 is a side view of FIG. 9;

FIG. 12-1 is a front view of FIG. 12;

FIG. 12-2 is a side view of FIG. 12;

FIG. 12-3 is a rear view of FIG. 12;

FIG. 12-4 is an A-A cross-sectional view of FIG. 12;

FIG. 12-5 is an enlarged view of region C in FIG. 12-4;

FIG. 12-6 is a B-B cross-sectional view of the flanges of a concave-convex position-limiting engagement structure in FIG. 12-4;

FIG. 13-1 is a schematic structural view of a rivet-type limiting mechanism;

FIG. 13-2 is a schematic structural view of a concave-convex engagement limiting mechanism;

FIG. 14-1 is a front view of FIG. 14;

FIG. 14-2 is a side view of FIG. 14;

FIG. 14-3 is a rear view of FIG. 14;

FIG. 14-4 is a schematic structural view of a warped end in FIG. 14;

FIG. 15-1 is a front view of FIG. 15;

FIG. 16-1 is a front view of FIG. 16;

FIG. 17-1 is an exploded view of FIG. 17.

FIG. 17-2 is a schematic structural view of mounting a hard palate connecting end in a first stage surgery of FIG. 17; and FIG. 17-3 is a schematic structural view of mounting a support in a second stage surgery of FIG. 17.

The meanings of the serial numbers in the above drawings are as follows: 1. hard palate connecting end, 2. support, 3. layered soft palate support of the present invention, 5. bone nail, 6. hard palate, 7. soft palate, 8. screw; 11. connecting structure on the hard palate connecting end and connected with the hard palate, 111. connecting through hole; 21. supporting plate, 211. warped end on the supporting plate; 22. through hole on the supporting plate; 23. blunt edge of the supporting plate, 231. spring segment, 232. flange of a concave-convex position-limiting engagement structure; 24. limiting mechanism, 241. lock nut, 242. lock screw, 243. limiting plate, 244. limiting groove; 25. adjustment mechanism, 251. wedge-shaped adjustment mechanism, 252. adjustment washer; 26. fixing rivet; β. lifting angle of the support, γ. sweepback angle of the warped end at the distal end of the support; L1. length of the hard palate connecting end, L2. length of the support (2), δ1. thickness of the near end of the support, δ2. thickness of the distal end of the support; R1. bending radius of the near end of the support, R2. bending radius of the distal end of the support; M. number of layers of supporting plates stacked at the near end of the soft palate support, N. number of layers of supporting plates stacked at the distal end of the soft palate support; P1. the first equal-length layer numbered from front to back of the layered structure of the support; P2. the second equal-length layer numbered from front to back of the layered structure of the support; P3. the third equal-length layer numbered from front to back of the layered structure of the support; P4. the fourth equal-length layer numbered from front to back of the layered structure of the support; P5. the fifth equal-length layer numbered from front to back of the layered structure of the support.

DETAILED DESCRIPTION OF THE INVENTION

Figure 15:
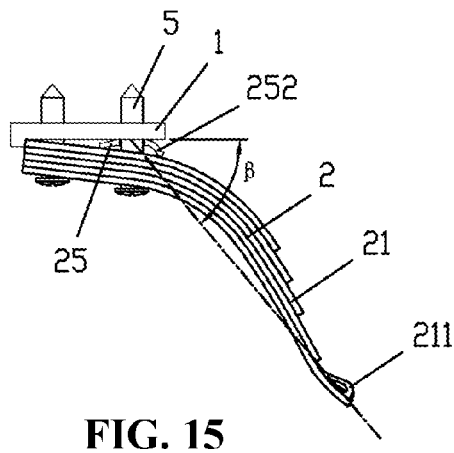
FIG. 15 is a schematic structural view of a removable layered soft palate support including an adjustment washer of the present invention.

The principle of treating OSAHS according to the present invention lies in that: supported by a hard palate 6, a support 2 inserted into a muscular layer of a soft palate is used to lift the collapsed soft palate 7, thereby achieving the objective of treating OSAHS. See FIG. 15 to FIG. 15-3.

Since the support 2 inserted into the muscular layer of the soft palate needs to swing along with the soft palate during swallowing, a high requirement is imposed on the fatigue resistance of the support 2. How to improve the fatigue resistance of the soft palate support 2 becomes a key to the improvement of the service life of the soft palate support 2.

In view of how to improve the fatigue resistance of the soft palate support 2, a technical solution of improving the fatigue life of the soft palate support is disclosed in the present invention, that is, a layered structure of supporting plates that is formed by stacking thin-walled plates is used as the support 2, which not only improves the adaptability of the support but also significantly improves the fatigue fracture resistance of the support while ensuring the supporting force.

When a single-layer titanium-nickel shape memory alloy sheet having a thickness of 0.6 mm after heat treatment is used as the soft palate support, the fatigue life is about $3 \times 10^6$ cycles, and calculated based on one swallow per minute, the fatigue life is about 5 years.

When the thickness decreases to 0.1 mm, and a 0.1 mm single-layer titanium-nickel shape memory alloy sheet after the same heat treatment process is used as the soft palate support, the fatigue life is about $5 \times 10^7$ cycles, and calculated based on one swallow per minute, the fatigue life is about 95 years.

When a Ti-based amorphous metal material, also referred to as Ti-based metallic glass, having a thickness of 0.1 mm is used, the fatigue life is greater than $1 \times 10^8$ cycles, and the fatigue life is about 190 years.

It can be seen that, the layered soft palate support formed by stacking thin-walled plates surely can meet clinical requirements.

Figure 1:
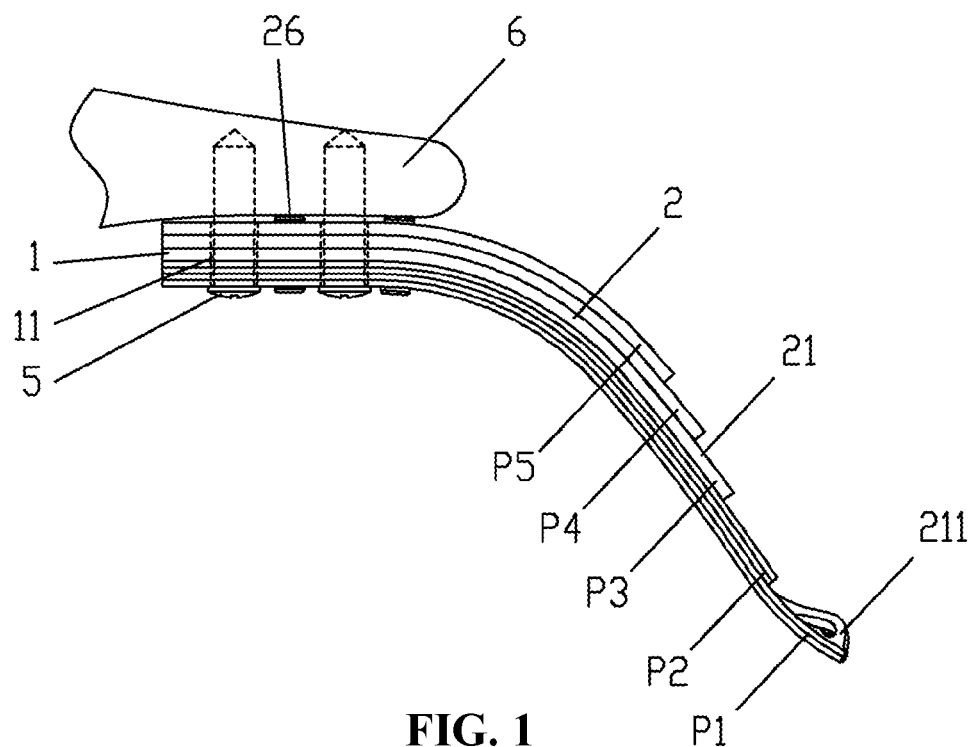
FIG. 1 is a schematic structural view of a layered soft palate support in a descending configuration of the present invention fixed to a hard palate.

Embodiment 1: A Layered Soft Palate Support in a Descending Configuration of the Present Invention Referring to FIG. 1, this embodiment shows a layered soft palate support in a descending configuration of the present invention.

For ease of description, it is defined that supporting plates 21 close to teeth are front supporting plates 21, supporting plates 21 close to a posterior pharyngeal wall are rear supporting plates 21, and supporting plates 21 of the same length are supporting plates 21 of an equal-length layer.

In this embodiment, the support 2 includes a total of five equal-length layers of supporting plates 21, namely, P1, P2, P3, P4 and P5 layers, where the P1 layer and the P2 layer are each formed by two layers of supporting plates 21. Each of the thin-walled supporting plates 21 of the P1 layer and the P2 layer has a thickness of 0.1 mm, and each of the thin-walled supporting plates 21 of the P3 layer, the P4 layer and the P5 layer has a thickness of 0.2 mm. In this way, the support 2 has an overall thickness δ1 of 1 mm at a near end, that is, close to the hard palate connecting end 1; and the support 2 has a thickness δ2 of 0.2 mm at a distal end. The support 2 has a length L2 of 30 mm.

A frontmost supporting plate 21 is the longest, a rearmost supporting plate 21 is the shortest, the lengths of the supporting plates 21 gradually decrease from front to back, and the layers of the supporting plates 21 have lengths satisfying P1>P2>P3>P4>P5, and are arranged in a descending order of length and sequentially stacked to form the layered soft palate support 2.

Figures 1, 14:
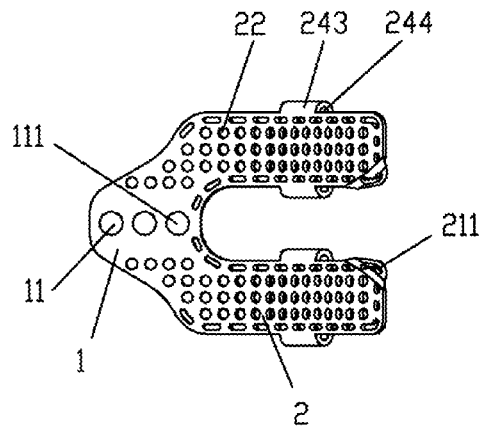
FIG. 14 is a three-dimensional schematic structural view of a layered soft palate support including a U-shaped slot type limiting mechanism of the present invention.
Figures 2, 14:
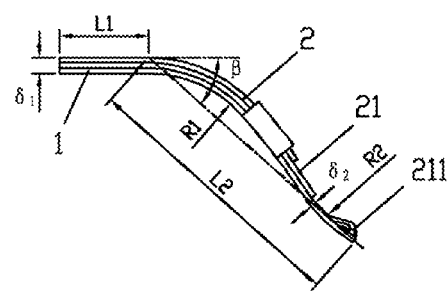
Figure 14:
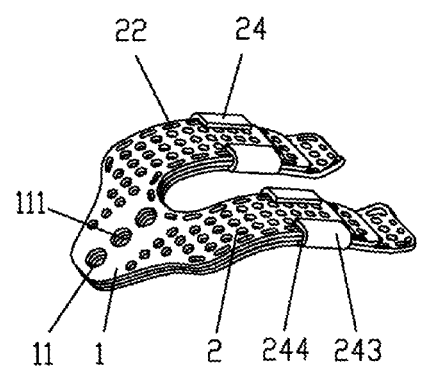
Figures 3, 14:
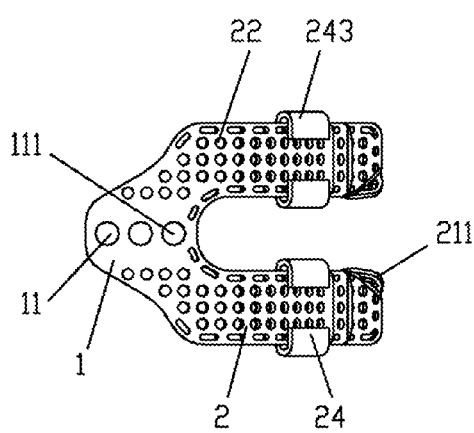
Figures 4, 14:
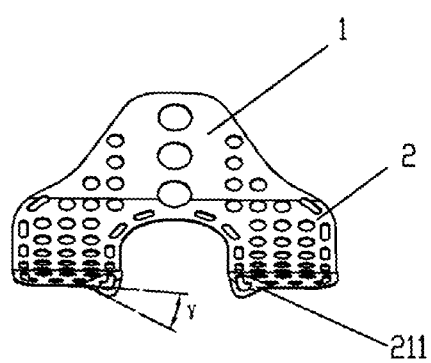

The geometrical shape and dimension of the layered soft palate support 3 of the present invention vary with different specific conditions of patients. See FIG. 14-1 and FIG. 14-4. Generally, the hard palate connecting end 1 has a length L1 of 5 to 30 mm, and the support 2 has a length L2 of 15 mm to 60 mm; a lifting angle β of the support 2, that is, an angle between a plane of the hard palate and a most distal end of the support 2, is 30° to 80°; a bending radius R1 of the near end of the support 2, that is, close to the hard palate connecting end 1, is 10 mm to 100 mm; a bending radius R2 of the distal end of the support 2, that is, away from the hard palate connecting end 1, is 20 mm to 120 mm; a sweepback angle γ of a warped end 211 at the distal end of the support 2, that is, an angle γ between a plane of the supporting plate 21 at the distal end of the support 2 and a plane of the warped end 211, is 0° to 75°, and preferably 20° to 50°; the near end of the support 2 has a thickness δ1 of 0.5 mm to 1.8 mm, and the distal end has a thickness δ2 of 0.1 mm to 0.8 mm.

The supporting plate 21 is a thin-walled plate made of a medical-purpose elastic material and having a curvature matching the shape of the soft palate, and the thin-walled plate has a thickness of 0.01 mm to 1.5 mm, and preferably 0.01 mm to 0.8 mm.

The medical-purpose elastic material of the supporting plate 21 is selected from a group consisting of amorphous alloy also referred to as metallic glass, titanium-zirconium-niobium alloy, titanium-nickel shape memory alloy, titanium and titanium alloy, medical grade stainless steel, medical grade elastic non-metallic materials, and other medical materials.

The most commonly used material is titanium-nickel shape memory alloy or amorphous alloy also referred to as metallic glass. The two materials both have excellent elasticity and excellent fatigue resistance, and metallic glass has superior fatigue resistance.

The used amorphous alloy is mainly selected from a group consisting of Ti-based amorphous metal materials, Zr-based amorphous metal materials, Nb-based amorphous metal materials, Fe-based amorphous metal materials and the like. The Ti-based amorphous metal material is a more preferable material for the soft palate support 2, and its fatigue life is greater than $1 \times 10^8$ cycles.

In addition, the supporting plate 21 is configured with through holes 22. The through holes 22 can facilitate growth and coverage of tissues, to effectively fix the supporting plate 21 into the muscular layer of the soft palate. See FIG. 14-1.

Figure 9:
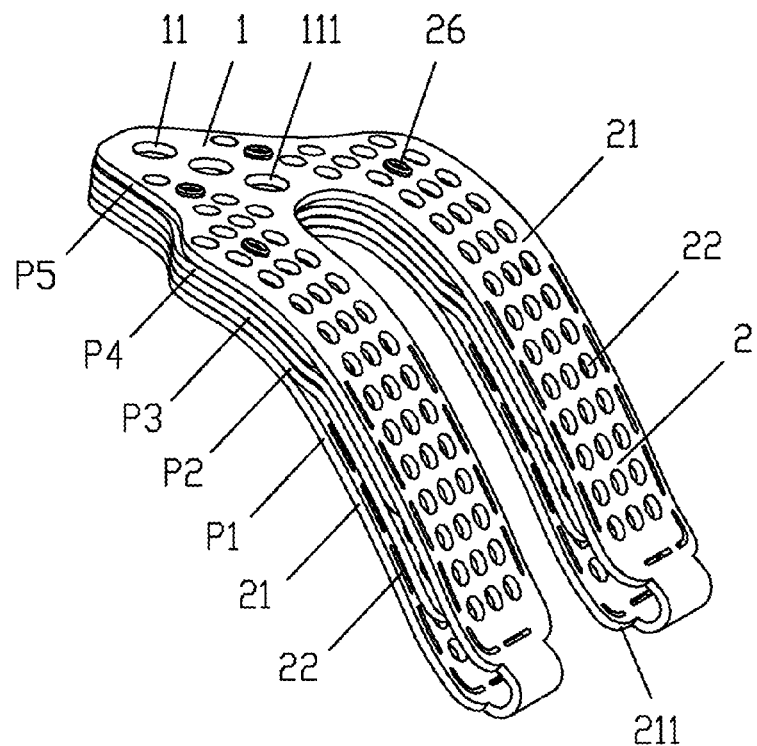
FIG. 9 is a three-dimensional schematic structural view of a U-shaped layered soft palate support in a sandwiched descending configuration of the present invention.
Figures 1, 9:
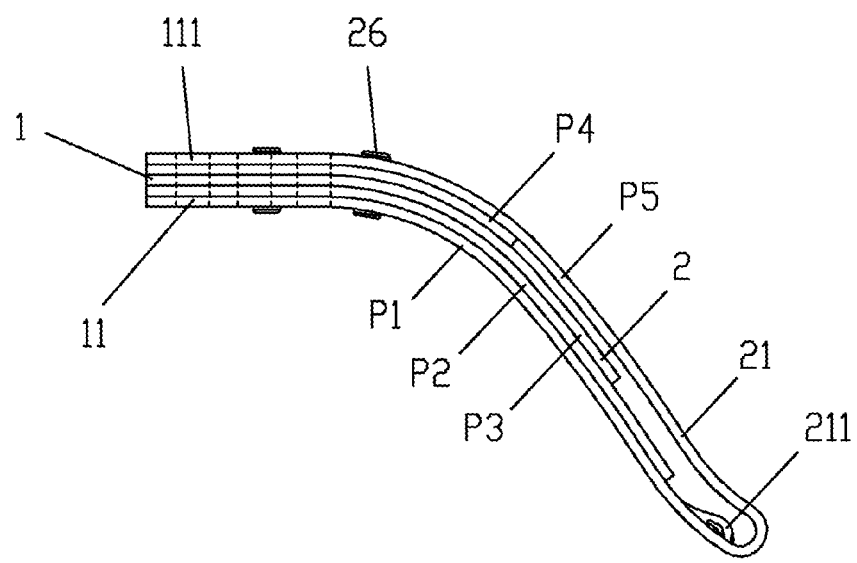

Generally, the hard palate connecting end 1 may be configured with a fixing rivet 26 for riveting the supporting plates 21, so as to facilitate clinical mounting and fixing. See FIG. 9 and FIG. 9-1.

In clinical use, a small incision is made at a junction of the soft palate 7 and the hard palate 6, and the support 2 is inserted into a muscular layer at a middle portion of the soft palate 7; and a medical bone nail 5 is passed through a through hole 111 on the hard palate connecting end 1 to fix the hard palate connecting end 1 to the hard palate 6.

During clinical implantation, the support 2 is inserted into the soft palate by a length equal to ⅕ to ⅘, and most preferably, ⅔ to ¾, of a total length of the soft palate.

Since the layered structure of supporting plates that is formed by stacking thin-walled plates is used as the support 2, not only the adaptability of the support is improved but also the fatigue fracture resistance of the support is significantly improved while ensuring the supporting force, and the fatigue life is greater than $1 \times 10^8$ cycles. Provided that the same material and process are adopted, the smaller the thickness of the supporting plates 21 forming the support 2 is, the longer the fatigue life is.

Figure 2:
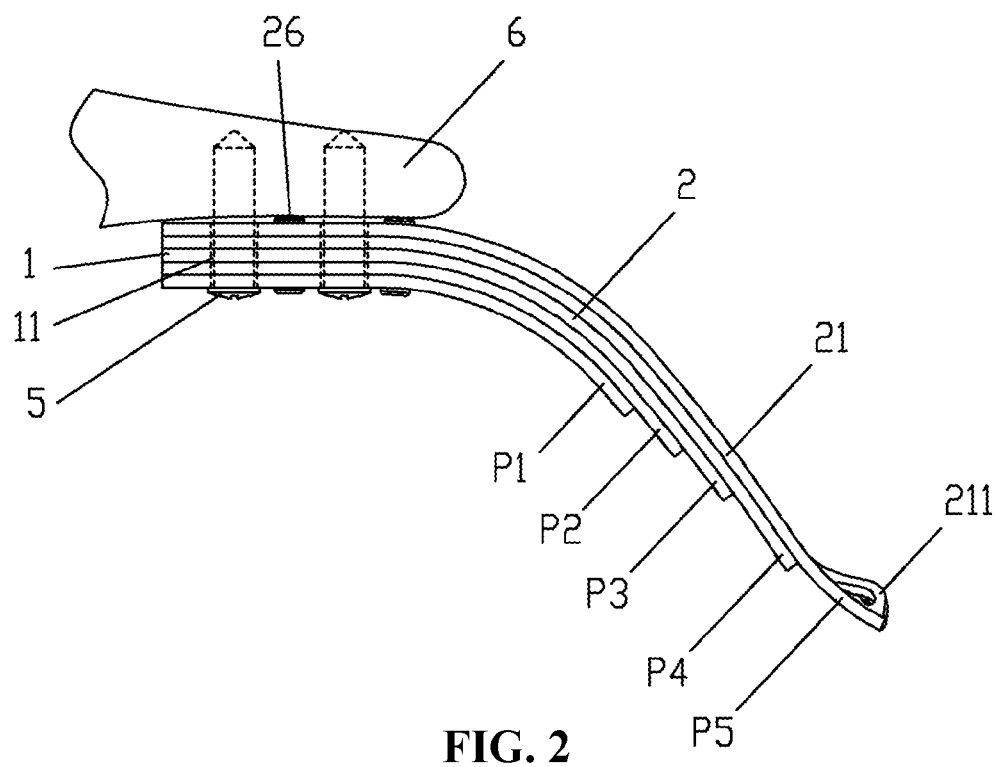
FIG. 2 is a schematic structural view of a layered soft palate support in an ascending configuration of the present invention fixed to a hard palate.

Embodiment 2: A Layered Soft Palate Support in an Ascending Configuration of the Present Invention Referring to FIG. 2, this embodiment is different from the above embodiment in that the stacking manner of the supporting plates 21 forming the support 2 is changed, and the lengths of the supporting plates 21 gradually increases from front to back, that is, P1<P2<P3<P4<P5, form a configuration in an ascending order of length. Another difference lies in that the supporting plates 21 have the same thickness.

In addition, the supporting plates 21 forming the support 2 may be stacked in various manners.

Figure 3:
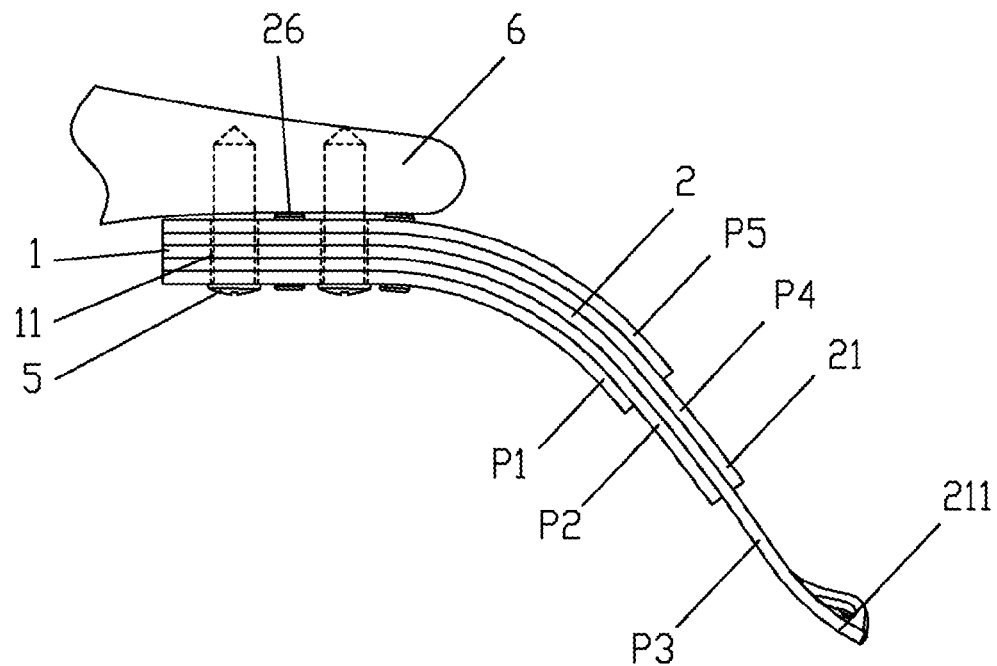
FIG. 3 is a schematic structural view of a layered soft palate support in a symmetric configuration of the present invention to a hard palate.

FIG. 3 shows a layered soft palate support in a symmetric configuration. In this embodiment, the length of the P1 layer is equal to the length of the P5 layer, the length of the P2 layer is equal to the length of the P4 layer, the P3 layer is the longest, and a symmetric configuration centered about the P3 layer is formed.

Figure 4:
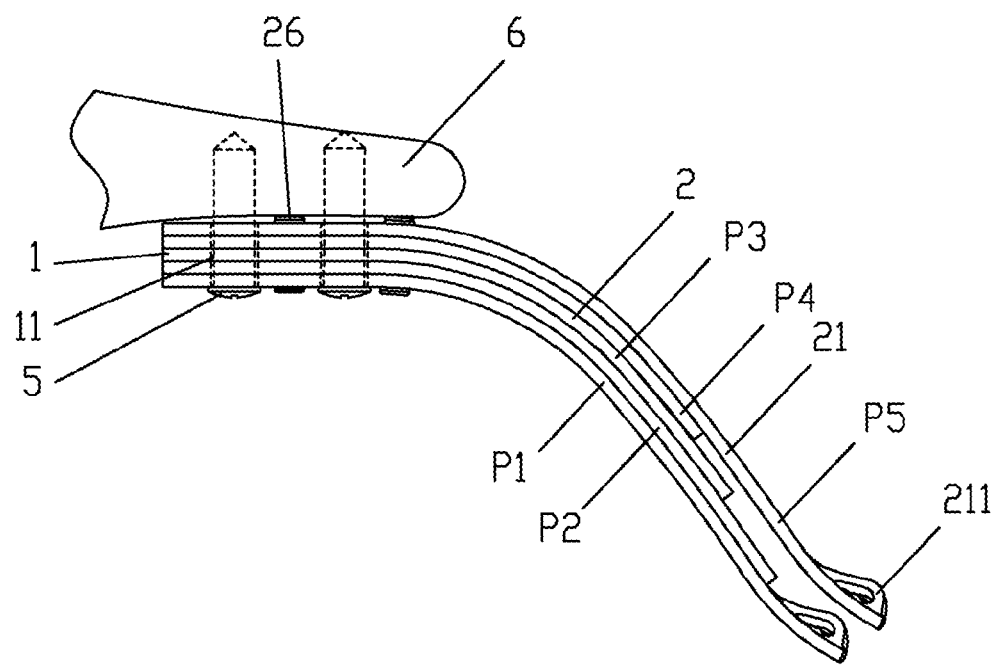
FIG. 4 is a schematic structural view of a layered soft palate support in a sandwiched descending configuration of the present invention fixed to a hard palate.

FIG. 4 shows a layered soft palate support in a sandwiched descending configuration. In this embodiment, the length of the P1 layer is equal to the length of the P5 layer, the intermediate three layers have lengths satisfying P2>P3>P4, and a descending configuration is formed.

Figure 5:
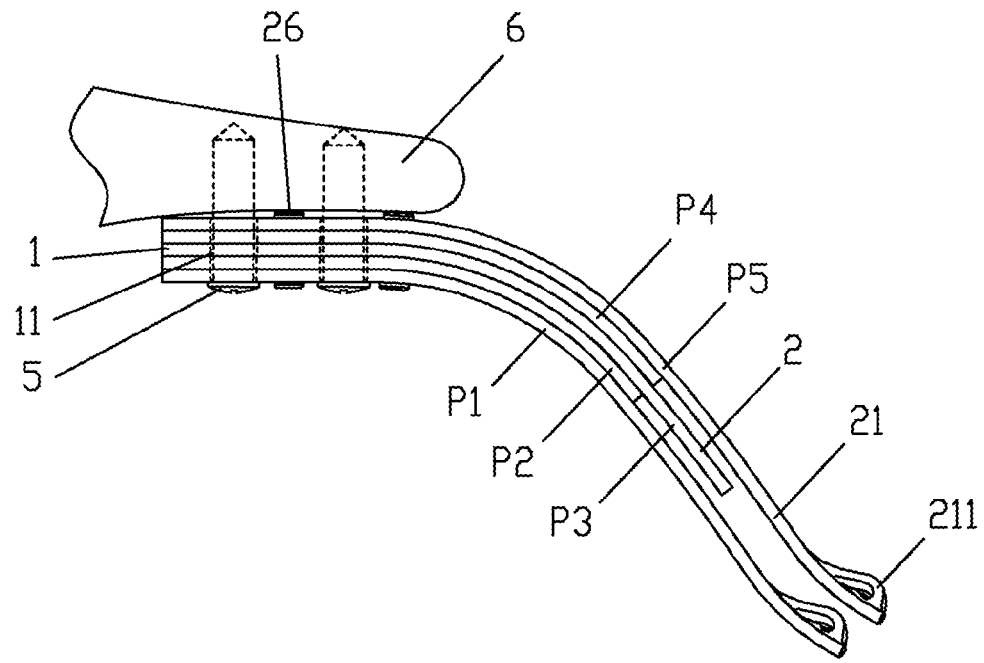
FIG. 5 is a schematic structural view of a layered soft palate support in a sandwiched symmetric configuration of the present invention fixed to a hard palate.

FIG. 5 shows a layered soft palate support in a sandwiched symmetric configuration. In this embodiment, the length of the P1 layer is equal to the length of the P5 layer, the intermediate three layers, the length of the P2 layer is equal to the length of the P4 layer, and a symmetric configuration centered about the P3 layer is formed.

Figure 6:
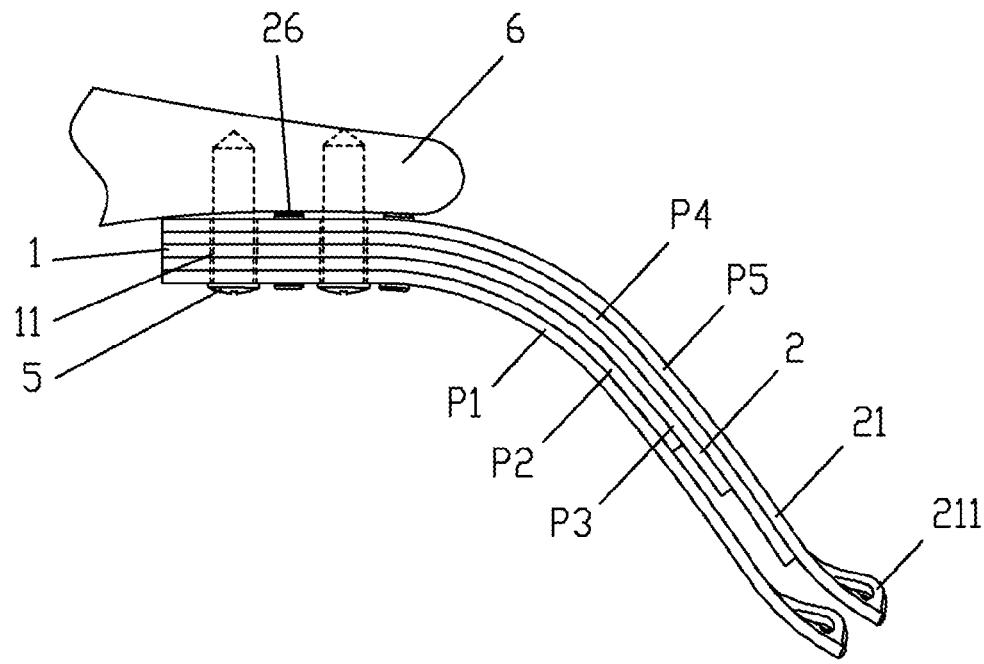
FIG. 6 is a schematic structural view of a layered soft palate support in a sandwiched ascending configuration of the present invention fixed to a hard palate.

FIG. 6 shows a layered soft palate support in a sandwiched ascending configuration. In this embodiment, the length of the P1 layer is equal to the length of the P5 layer, the intermediate three layers have lengths satisfying P2<P3<P4, and an ascending configuration is formed.

Among the numerous configurations, the soft palate supports of the descending configuration and the sandwiched symmetric configuration are preferred.

In addition, in these embodiments, five equal-length layers are adopted, which is for ease of description. For actual product manufacturing, the layered structure forming the support 2 may also be one equal-length layer, two equal-length layers, three equal-length layers, four equal-length layers, or the like. Each of the equal-length layers may be formed by stacking one or more thin-walled supporting plates 21.

Figure 7:
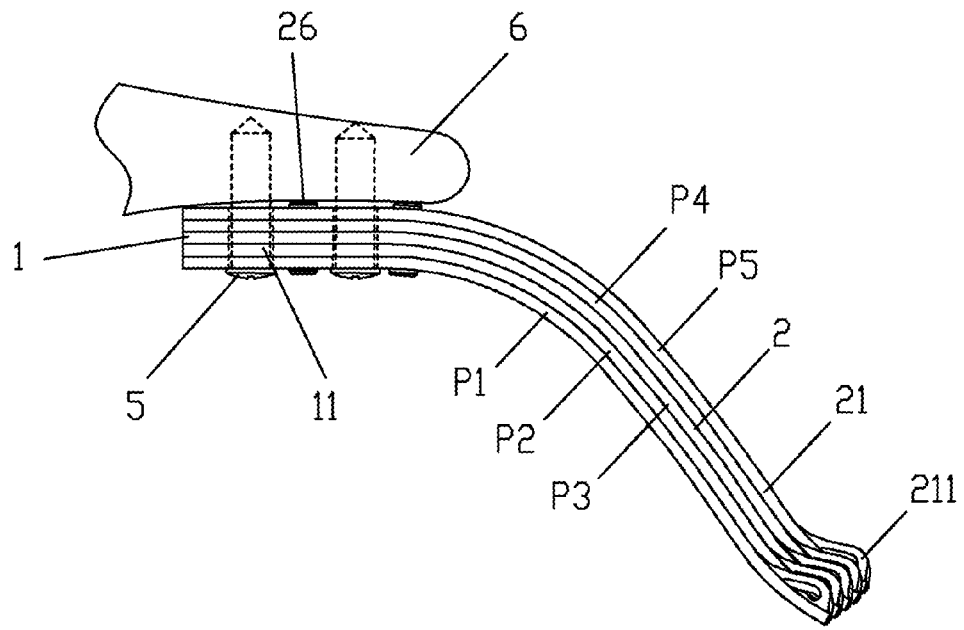
FIG. 7 is a schematic structural view of a layered soft palate support with one equal-length layer of the present invention.

FIG. 7 shows a layered soft palate support with one equal-length layer of the present invention. In this embodiment, five thin-walled supporting plates 21 of the same length are stacked to form the support 2, where each of the thin-walled supporting plates 21 has a thickness of about 0.12 mm.

Figure 8:
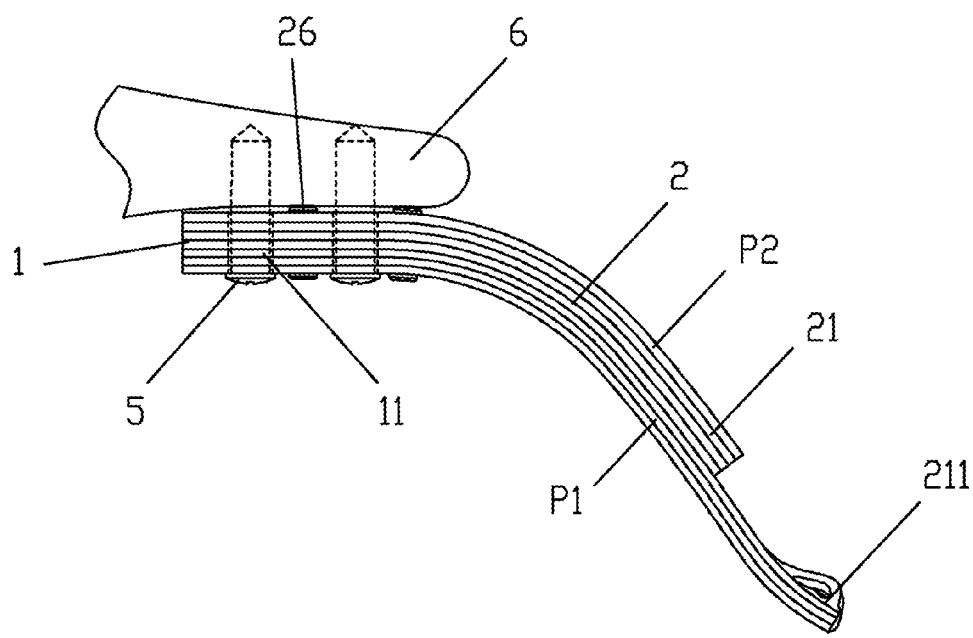
FIG. 8 is a schematic structural view of a layered soft palate support with two equal-length layers of the present invention.

FIG. 8 shows a layered soft palate support with two equal-length layers of the present invention. In this embodiment, the P1 layer is formed by three thin-walled supporting plates 21 of the same length, the P2 layer is formed by four thin-walled supporting plates 21 of the same length, and the P1 layer and the P2 layer are stacked to form the support 2, where each of the thin-walled supporting plates 21 has a thickness of about 0.08 mm.

Embodiment 3: A U-Shaped Layered Soft Palate Support in a Sandwiched Descending Configuration of the Present Invention Referring to FIG. 9 and FIG. 9-1, in this embodiment, the frontmost supporting plate 21 of the P1 layer and the rearmost supporting plate 21 of the P5 layer are formed by bending a single thin-walled metal plate into a U-shape, the supporting plates 21 of the intermediate P2, P3 and P4 layers are sequentially arranged in a descending order of length. The advantage of such a design lies in that swinging of the supporting plate 21 is limited between the frontmost P1 layer and the rearmost P5 layer, so that the supporting force of the support 2 can be increased without compromising the adaptability.

Figure 10:
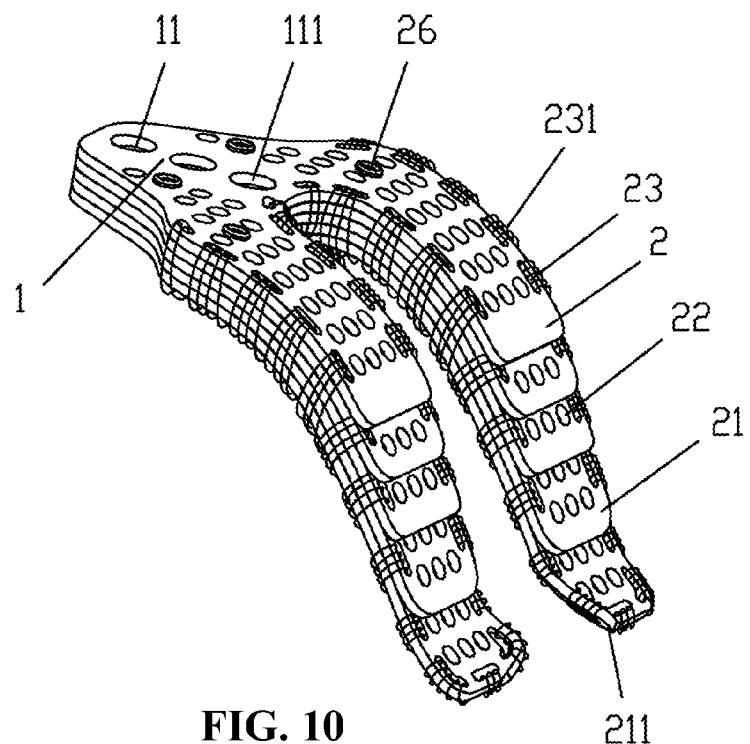
FIG. 10 is a three-dimensional schematic structural view of a layered soft palate support with a blunt edge being a single wire-wound coil spring of the present invention.

Embodiment 4: A Layered Soft Palate Support with a Blunt Edge being a Coil Spring of the Present Invention Referring to FIG. 10, in this embodiment, the support 2 includes a blunt edge 23. The blunt edge 23 is a single wire-wound coil spring. The coil spring passes through the through holes 22 at an edge of the supporting plate 21, to connect the supporting plates 21 of the layers, which on one hand prevents excessive separation of the supporting plates 21 of the layers during swinging of the support 2, and on the other hand provides a function of blunting the edge of the support 2, thereby facilitating fixation and growth of tissues.

The blunt edge 23 being the coil spring is movably wound in the through holes 22 at the edge of the supporting plate 21, so that a gap between the supporting plates 21 of the layers is maintained in a reasonable range, where the gap is generally smaller than 0.6 mm.

Figure 11:
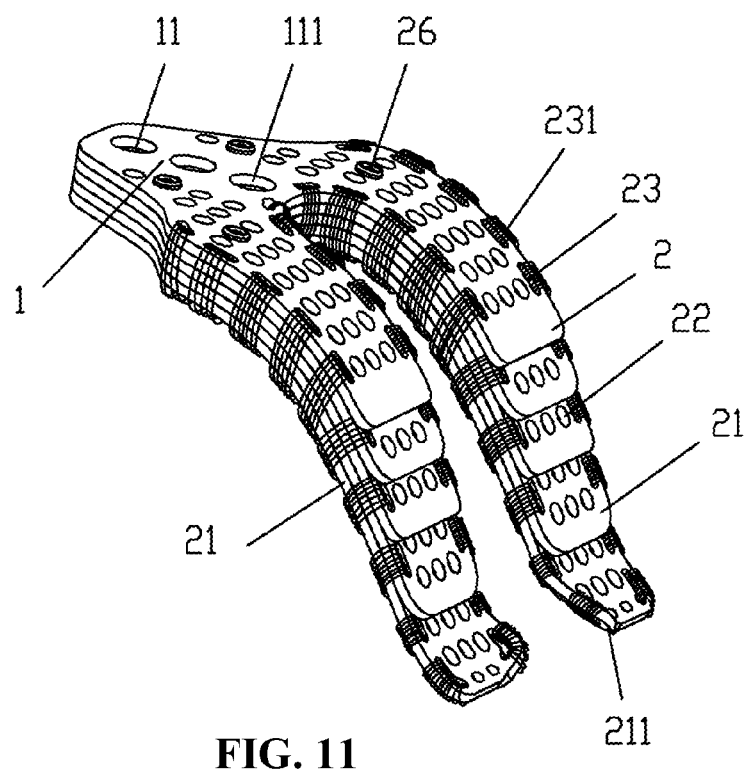
FIG. 11 is a three-dimensional schematic structural view of a layered soft palate support with a blunt edge being a coil spring segment of the present invention.

The coil spring may be wound in different manners. FIG. 11 shows a segmented winding manner, where multiple segments of metal wires are used to connect the supporting plates 21 of the layers at different positions.

When the blunt edge 23 adopts the coil spring structure, the blunt edge 23 of the coil spring structure may be made of a medical grade metal wire selected from a group consisting of medical grade stainless steel wires, medical titanium metal wires, medical grade titanium-nickel shape memory alloy, medical grade amorphous alloy wires and wires of other metal materials, or may be made of various high-strength medical polymer material threads or films.

Figures 1, 12:
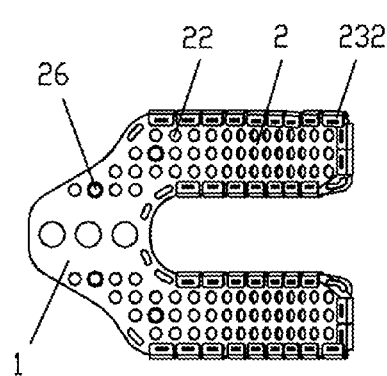
FIG. 12 is a three-dimensional schematic structural view of a layered soft palate support with a blunt edge being flanges of a concave-convex position-limiting engagement structure of the present invention.
Figure 12:
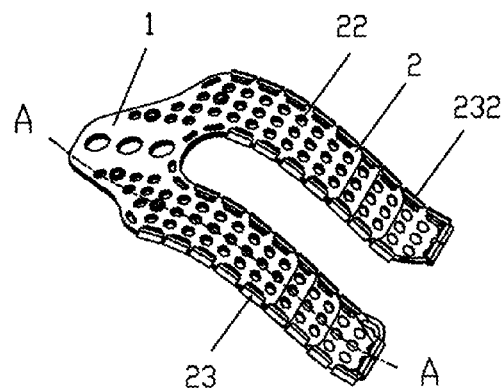
Figures 2, 12:
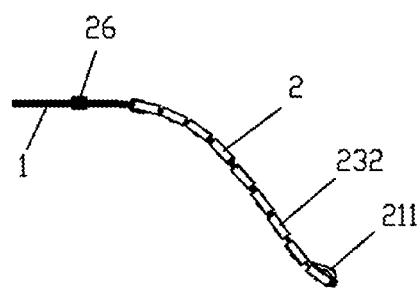
Figures 4, 12:
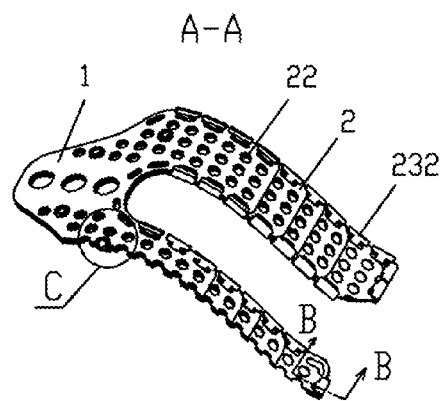
Figures 3, 12:
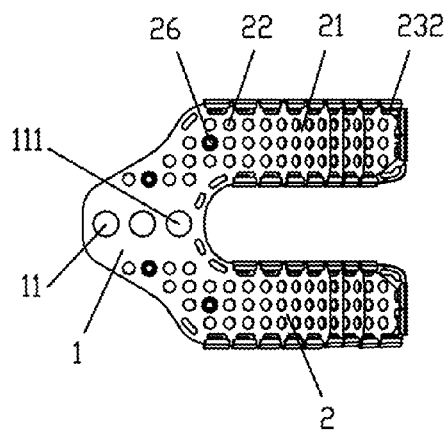
Figures 5, 6, 12:
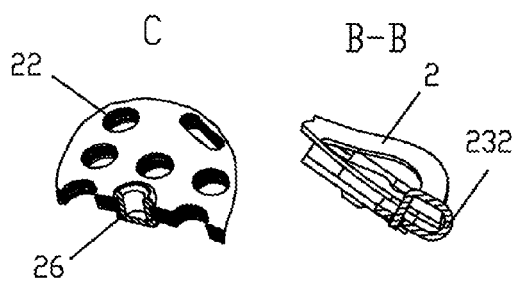

Embodiment 5: A Layered Soft Palate Support with a Blunt Edge being Flanges of a Concave-Convex Position-Limiting Engagement Structure Referring to FIG. 12 to FIG. 12-6, in this embodiment, the blunt edge 23 on the support 2 is tiny flanges 232 of a concave-convex position-limiting engagement structure. The tiny flanges 232 of a concave-convex position-limiting engagement structure are discontinuously distributed, and fixed to the edge of the support 2 to connect the supporting plates 21 of the layers.

Figure 13:
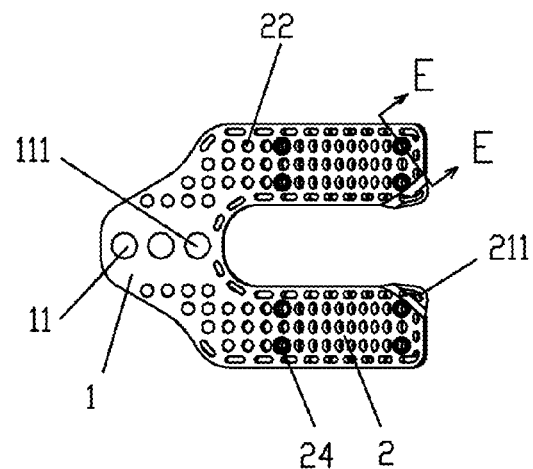
FIG. 13 is a schematic structural view of a layered soft palate support including a position-limiting mechanism of the present invention.
Figures 1, 2, 13:
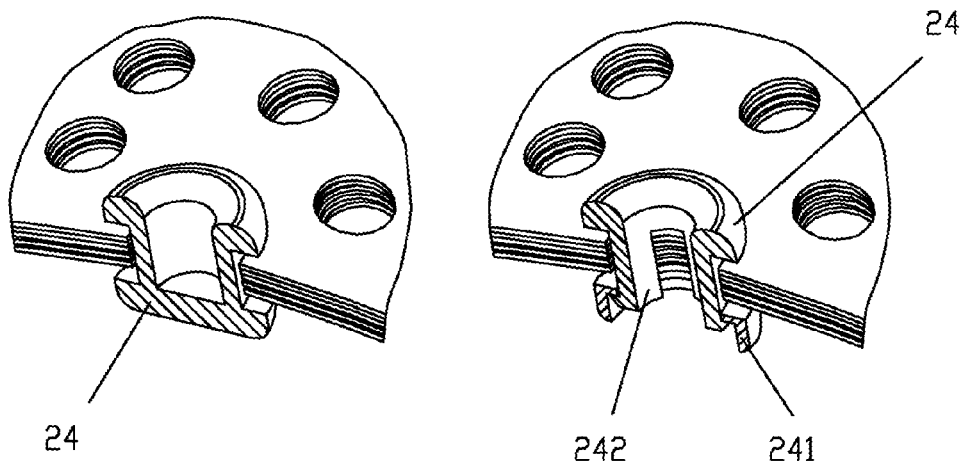

Embodiment 6: A Layered Soft Palate Support Including a Position-Limiting Mechanism of the Present Invention Referring to FIG. 13 to FIG. 13-2, in this embodiment, the support 2 includes a position-limiting mechanism 24. The provision of the position-limiting mechanism 24 is to prevent excessive separation of the supporting plates 21 of the layers during swinging of the support 2, that is, to control the gap between the supporting plates 21 of the layers. The simplest and most effective method is adopting a rivet-type limiting structure, that is, fixing the supporting plates 21 of the layers by using a rivet. See FIG. 13-1. The objective of controlling the gap between the supporting plates 21 of the layers may also be achieved through a concave-convex position-limiting engagement structure. A protruding lock screw 242 is embedded in a recessed lock nut 241 to form a concave-convex engagement limiting mechanism 24, which can control the gap between the supporting plates 21 of the layers. See FIG. 13-2.

Embodiment 7: A Layered Soft Palate Support Including a U-Shaped Slot Type Limiting Structure of the Present Invention Referring to FIG. 14 to FIG. 14-4, in this embodiment, the support 2 is configured with a position-limiting mechanism 24. The limiting mechanism 24 is formed by a limiting groove 244 and a limiting plate 243. The limiting plate 243 is part of an edge of one of the supporting plates 21, and is bent to form a rectangular or U-shaped slot opening serving as the limiting groove 244.

Embodiment 8: A Removable Layered Soft Palate Support Including an Adjustment Washer of the Present Invention Referring to FIG. 15 to FIG. 15-1, this embodiment shows a removable layered soft palate support including an adjustment washer of the present invention. The hard palate connecting end 1 is removably assembled to the support 2. By removing the bone nail 5, the support 2 can be detached from the hard palate connecting end 1; and by tightening the bone nail 5, the support 2 can be fixed to the hard palate connecting end 1, and then fixed to the hard palate 6 together with the hard palate connecting end 1.

In this embodiment, an adjustment washer 252 is further configured. By appropriately loosening the bone nail 5 at the distal end, the height of the adjustment washer 252 is increased, the lifting angle $\beta$ of the support 2 is increased, and the lifting degree of the soft palate 7 is increased; by appropriately tightening the bone nail 5 at the distal end, the height of the adjustment washer 252 is reduced, the lifting angle $\beta$ of the support 2 is reduced, and the lifting degree of the soft palate 7 is reduced. In this way, the lifting degree of the soft palate 7 by the support 2 can be adjusted within a certain range, thereby facilitating clinical mounting.

Figure 16:
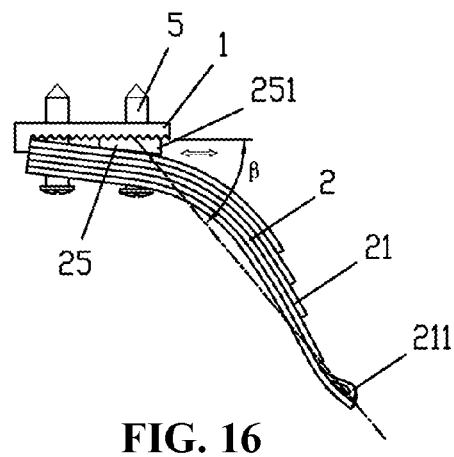
FIG. 16 is a schematic structural view of a removable layered soft palate support including a wedge-shaped adjustment mechanism of the present invention.
Figures 1, 15:
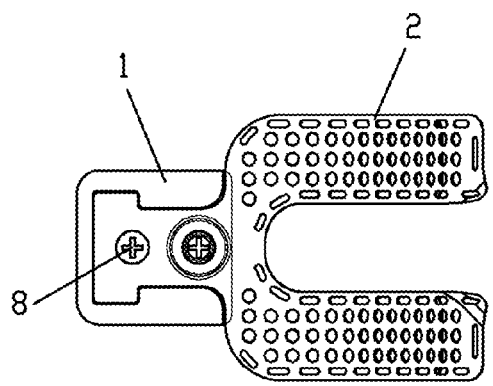
Figures 1, 16:
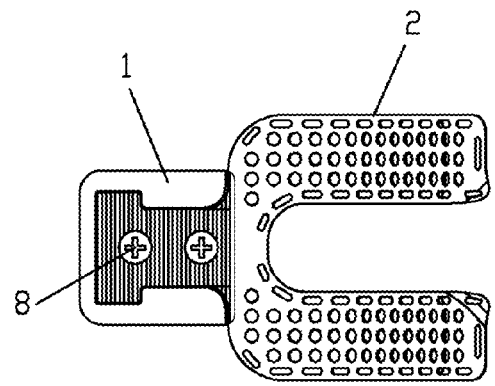

Embodiment 9: A Removable Layered Soft Palate Support Including a Wedge-Shaped Adjustment Mechanism of the Present Invention Referring to FIG. 16 to FIG. 16-1, this embodiment shows a removable layered soft palate support including a wedge-shaped adjustment mechanism of the present invention. The hard palate connecting end 1 is removably assembled to the support 2. By removing the bone nail 5, the support 2 can be detached from the hard palate connecting end 1; and by tightening the bone nail 5, the support 2 can be fixed to the hard palate connecting end 1, and then fixed to the hard palate 6 together with the hard palate connecting end 1.

In this embodiment, a wedge-shaped adjustment mechanism 251 is further configured. By appropriately loosening the bone nail 5 at the distal end, the wedge-shaped adjustment mechanism 251 is pushed toward the near end, the lifting angle $\beta$ of the support 2 is increased, and the lifting degree of the soft palate 7 is increased; by appropriately tightening the bone nail 5 at the distal end, the wedge-shaped adjustment mechanism 251 is pushed toward the distal end, the lifting angle $\beta$ of the support 2 is reduced, and the lifting degree of the soft palate 7 is reduced. In this way, the lifting degree of the soft palate 7 by the support 2 can be adjusted within a certain range, thereby facilitating clinical mounting.

In addition, the adjustment mechanism 25 may be designed in various ways, and is merely described by way of example herein.

Figure 17:
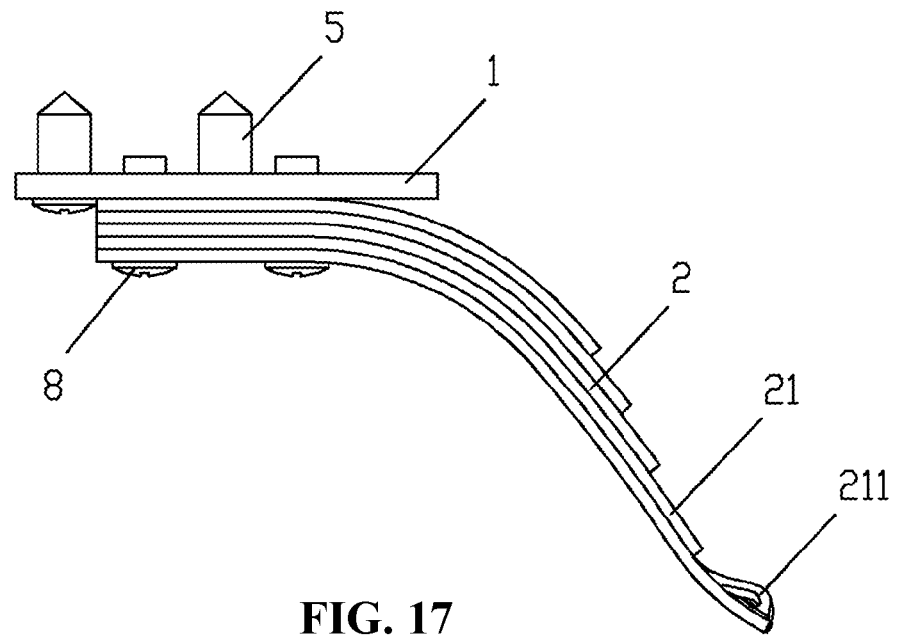
FIG. 17 is a schematic structural view of a soft palate support of the present invention capable of being implanted in stages after being assembled.
Figures 1, 17:
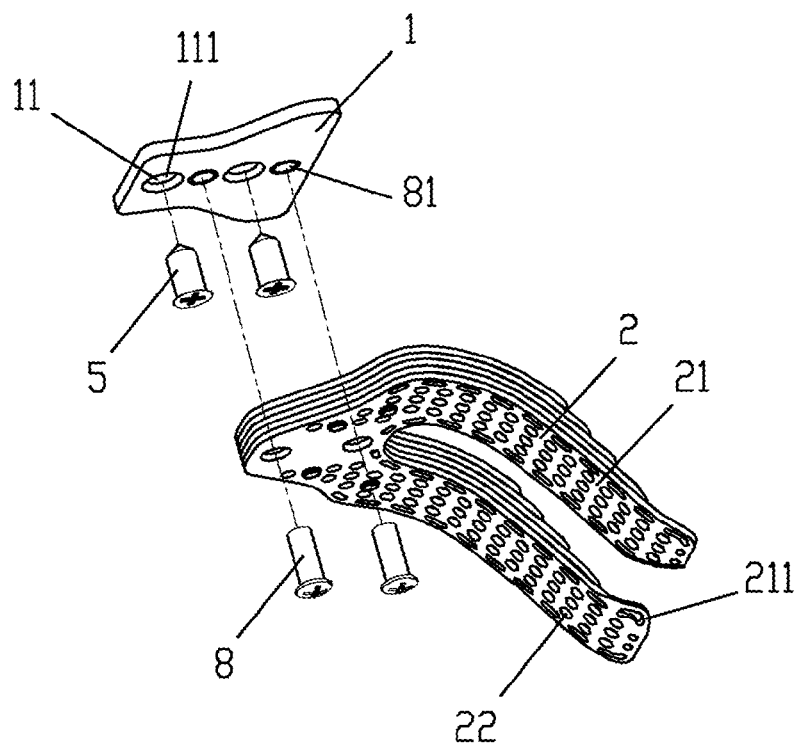
Figures 2, 17:
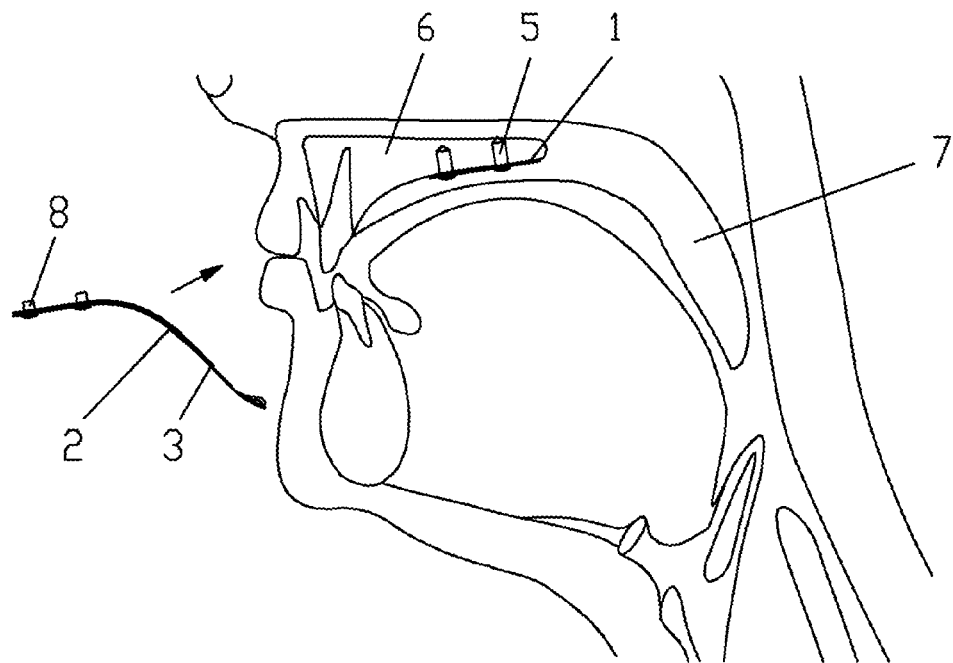
Figures 3, 17:
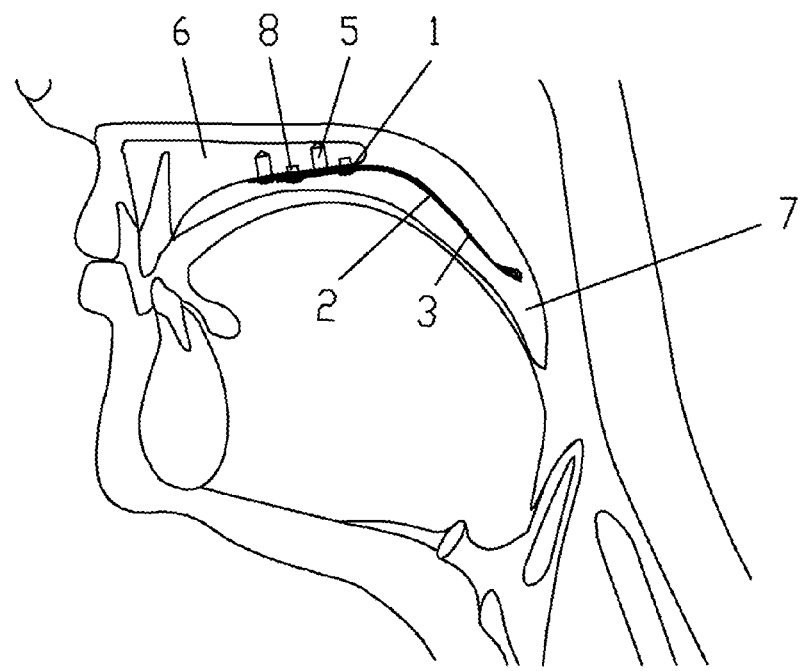

Embodiment 10: A Removable Layered Soft Palate Support Including a Wedge-Shaped Adjustment Mechanism of the Present Invention Referring to FIG. 17 to FIG. 17-3, this embodiment shows a soft palate support of the present invention capable of being implanted in stages. The hard palate connecting end 1 may be fixed to the hard palate 6 through a bone nail 5, and the support 2 is removably assembled to the hard palate connecting end 1 through a screw 8.

In a clinical surgery, the support may be implanted in two stages.

First stage surgery: Under local anesthesia or general anesthesia, first a small incision is made at a proper portion of the hard palate 6, and then the hard palate connecting end 1 of the layered soft palate support is implanted, the bone nail 5 is passed through the through hole 111 on the hard palate connecting end 1 to fix the hard palate connecting end 1 to the hard palate 6, and the incision is sutured. See FIG. 17-2.

Second stage surgery: One month to three months later after the first stage surgery is finished, the hard palate connecting end 1 has been firmly fixed to the hard palate 6. At this time, a second stage surgery is performed. Under local anesthesia or general anesthesia, a small incision is made at the junction of the soft palate 7 and the hard palate 6, and then one end of the support 2 is inserted into the muscular layer at the middle portion of the soft palate 7, where the support 2 is inserted into the soft palate by a length equal to 1/5 to 4/5 of the total length of the soft palate; and then, the other end of the support 2 is fixed to the hard palate connecting end 1 by using the screw 8, and the incision is sutured. See FIG. 17-3.

It should be noted that, the structures disclosed and described in the present invention may be replaced by other structure with the same effect, and the embodiments described in the present invention are not intended to limit the present invention. Though the preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

What is claimed:

1. A layered soft palate support for implantation into a human body, comprising:
    a layered structure formed by two or more supporting plates, each supporting plate having a hard palate connecting end and a soft palate insertion end, wherein the soft palate insertion end is configured for insertion into a soft palate, and the hard palate connecting end is configured to be fixed to a hard palate;
    wherein at least two of the two or more supporting plates have distinct lengths with respect to a longitudinal axis.

2. The layered soft palate support according to claim 1, wherein the layered soft palate support comprises a blunt edge.

3. The layered soft palate support according to claim 2, wherein the blunt edge is a coil spring structure, wound in through holes at an edge of the supporting plate, to connect the supporting plates.

4. The layered soft palate support according to claim 3, wherein the blunt edge comprises more than one coil spring segment, wound in through holes of the supporting plate, to connect the supporting plates.

5. The layered soft palate support according to claim 2, wherein the blunt edge is flanges of a concave-convex position-limiting engagement structure.

6. The layered soft palate support according to claim 1, wherein the layered soft palate support comprises an adjustment mechanism capable of adjusting a degree of curvature of the two or more supporting plates.

7. The layered soft palate support according to claim 6, wherein:
    the adjustment mechanism is a wedge-shaped adjustment mechanism;
    the degree of curvature of the soft palate support is increased when the wedge-shaped adjustment mechanism is moved toward a near end, so as to increase a lifting degree of the soft palate; and
    the degree of curvature of the soft palate support is reduced when the wedge-shaped adjustment mechanism is moved toward a distal end, so as to reduce the lifting degree of the soft palate.

8. The layered soft palate support according to claim 6, wherein:
    the adjustment mechanism is an adjustment washer;
    the degree of curvature of the soft palate support is increased when a height of the adjustment washer is increased, so as to increase a lifting degree of the soft palate; and
    the degree of curvature of the soft palate support is reduced when the height of the adjustment washer is reduced, so as to reduce the lifting degree of the soft palate.

9. The layered soft palate support according to claim 1, wherein the supporting plates of the layered structure are arranged in a sandwiched configuration such that a length of a frontmost supporting plate is substantially equal to a length of a rearmost supporting plate, and supporting plates between the frontmost supporting plate and rearmost supporting plate are sequentially arranged in a descending order of length, are symmetrically arranged, or are sequentially arranged in an ascending order of length.

10. The layered soft palate support according to claim 9, wherein when the supporting plates are arranged in a sandwiched configuration such that the frontmost supporting plate and the rearmost supporting plate are formed by bending a single plate into a U-shape, and the supporting plates in between the frontmost supporting plate and rearmost supporting plate are sequentially arranged in a descending order of length, are symmetrically arranged, or are sequentially arranged in an ascending order of length.

11. The layered soft palate support according to claim 1, wherein:
    the layered soft palate support comprises a position-limiting mechanism for limiting a distance between the two or more supporting plates of the layered support such that the supporting plates are constrained by the position-limiting mechanism, and
    the two or more supporting plates having a variable degree of curvature.

12. The layered soft palate support according to claim 11, wherein the position-limiting mechanism is formed by a limiting groove and a limiting plate, and the limiting plate is part of an edge of one of the supporting plates and is bent to form a rectangular or U-shaped slot opening serving as the limiting groove.

13. The layered soft palate support according to claim 1, wherein each supporting plate is a thin-walled plate made of a medical-purpose elastic material and having a curvature matching a shape of the soft palate.

14. The layered soft palate support according to claim 1, wherein:
    a first one of the supporting plates has a length that is greater than a length of a second one of the supporting plates,
    the first supporting plate has a wall thickness that is smaller than a wall thickness of the second supporting plate, and the first supporting plate has an amplitude of swing that is greater than an amplitude of swing of the second supporting plate.

15. The layered soft palate support according to claim 1, wherein a number M of layers of the stacked thin-walled supporting plates at a near end of the layered soft palate support that is close to the hard palate connecting end, is greater than a number N of layers of the stacked thin-walled supporting plates at a distal end of the layered soft palate support that is remote from the hard palate connecting end.

16. The layered soft palate support according to claim 1, wherein the supporting plates are sequentially arranged in a descending order of length such that a supporting plate that is shortest among the two or more supporting plates is arranged closest to the hard palate at the hard palate connecting end.

17. The layered soft palate support according to claim 1, wherein the supporting plates are sequentially arranged in an ascending order of length such that a supporting plate that is shortest among the two or more supporting plates is arranged farthest from the hard palate at the hard palate connecting end.

18. The layered soft palate support according to claim 1, wherein the hard palate connecting end has a length L1 of 5 to 30 mm, the soft palate support has a length L2 of 15 mm to 60 mm, and a lifting angle β of the soft palate support is 30° to 80°, wherein the lifting angle is an angle between a plane of the hard palate and a most distal end of the soft palate support.

19. The layered soft palate support according to claim 1, wherein a bending radius R1 of a near end of the soft palate support close to the hard palate connecting end is 10 mm to 100 mm; a bending radius R2 of a distal end of the soft palate support away from the hard palate connecting end is 20 mm to 120 mm; and the near end of the soft palate support has a thickness δ1 of 0.5 mm to 1.8 mm, and the distal end of the soft palate support has a thickness δ2 of 0.1 mm to 0.8 mm.

20. The layered soft palate support according to claim 1, wherein a sweepback angle γ of a warped end at a distal end of the soft palate support is 0° to 75°, wherein the sweepback angle is an angle between a plane of the two or more supporting plates at the distal end of the soft palate support and a plane of the warped end.

* * * * *